(12) United States Patent
Greenbaum

(10) Patent No.: US 12,128,172 B2
(45) Date of Patent: Oct. 29, 2024

(54) DOSAGE FORMS, PACKAGING, AND VAPORIZATION DEVICE FOR VAPORIZABLE FORMULATIONS

(71) Applicant: Resurgent Biosciences, Inc., Minneapolis, MN (US)

(72) Inventor: Eric Greenbaum, Denver, CO (US)

(73) Assignee: Resurgent Biosciences. Inc, Minneapolis, MN (US)

( * ) Notice: Subject to any disclaimer, the term of this patent is extended or adjusted under 35 U.S.C. 154(b) by 994 days.

(21) Appl. No.: 17/116,464

(22) Filed: Dec. 9, 2020

(65) Prior Publication Data

US 2021/0162143 A1    Jun. 3, 2021

Related U.S. Application Data

(63) Continuation of application No. PCT/US2019/036385, filed on Jun. 10, 2019.

(60) Provisional application No. 62/682,927, filed on Jun. 9, 2018.

(51) Int. Cl.
*A61M 11/04* (2006.01)
*A61M 15/00* (2006.01)

(52) U.S. Cl.
CPC ...... *A61M 11/041* (2013.01); *A61M 15/0048* (2014.02); *A61M 15/005* (2014.02)

(58) Field of Classification Search
CPC .... A61M 11/041–042; A61M 15/0028; A61M 15/0045–0051; A61M 15/0061–0063; A61M 15/06; A24F 40/00; A24F 40/10–42; A24F 47/00
See application file for complete search history.

(56) References Cited

U.S. PATENT DOCUMENTS

| | | | |
|---|---|---|---|
| 2012/0248005 A1* | 10/2012 | Bergey | B65D 75/327 156/69 |
| 2013/0087144 A1* | 4/2013 | Todd | A61M 15/0081 128/203.14 |
| 2017/0360861 A1 | 12/2017 | Humphreys et al. | |
| 2018/0043115 A1 | 2/2018 | Gould et al. | |
| 2020/0281271 A1* | 9/2020 | Wilson | A24F 40/48 |

OTHER PUBLICATIONS

Search Report and Written Opinion for PCT/US2019/036385 mailed on Oct. 18, 2019.

(Continued)

*Primary Examiner* — Rachel T Sippel
(74) *Attorney, Agent, or Firm* — Dicke, Billig & Czaja, PLLC

(57) ABSTRACT

A single dose vaporizable formulation including room temperature solid extracts and other botanical extracts and methods of processing and packaging single dose portions of vaporizable formulations. Also, methods of dispensing single dose portions, including segmented dose formulations and applicator-tab devices for vaporizers. A vaporizer having a heating chamber element with an indentation or cavity sized to receive a similarly-shaped, single dose vaporizable formulation.

18 Claims, 18 Drawing Sheets

(56) References Cited

OTHER PUBLICATIONS

NCV Newswire. "Pure Ratios Introduces Novel Patented Sustained-Release CBD and THC Lozenges", picture of Pure Ratio Sustained Release CBD and THC lozenges. (https://www.newcannabaisventures.com/pure-ratios-introduces-novel-patented-sustained-release-cbd-and-the-lozenges, Nov. 15, 2016, 1-6.

Hahn, et al., «Electronic Cigarettes: Overview of chemical composition and exposure estimation.», Tobacco Induced Diseases, BioMed Central, p. 10-12 and Table 4. (www.ncbi.nlm.nih.gov/pmc/articles/PMC4304610/#.), Dec. 9, 2014, 1-23.

\* cited by examiner

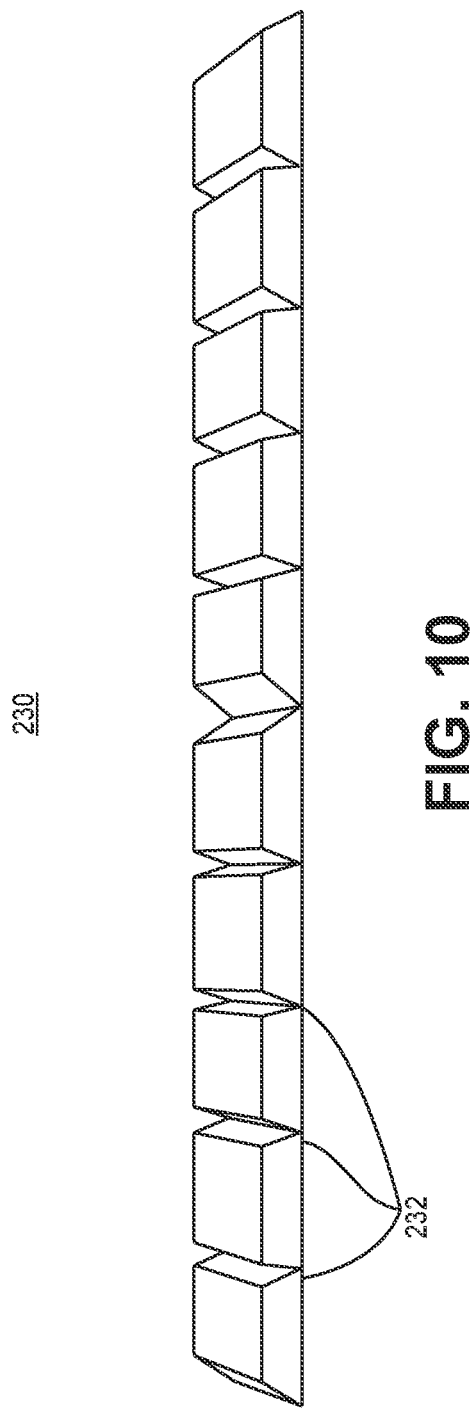

DOSAGE FORMS, PACKAGING, AND VAPORIZATION DEVICE FOR VAPORIZABLE FORMULATIONS

FIELD OF THE INVENTION

The invention relates generally to products, systems, processes, devices, and methods for providing individual use portions of vaporizable formulations.

BACKGROUND OF THE INVENTION

As more and more states legalize cannabis use for medical and recreational purposes new formulation and product types have risen in popularity. One such product type can generally be classified as extracts or concentrates. These extracts include product formulations referred to as "shatter," "wax," "budder," "resin," "rosin," "live resin," "sugar," "honeycomb," and the like. There are generally some significant differences between these different extract types in the areas of physical characteristics and chemical composition. Some of these extracts are solid or semisolid at room temperature. Some extracts (hereinafter "oils") are liquid at room temperature. Some extracts, such as "live resins" or "sauces" typically comprise a solid, portion mixed with a liquid portion—often THCA crystals in a high-terpene liquid.

Typically, cannabis extract are provided in a package wherein the entirety of the extract is in a single mass. For budders, waxes, crumbles, and the like this is often in a small jar. Shatters and the like are often provided folded up in a piece of parchment paper which is then enclosed in an envelope. Packaging of extract in this manner presents several problems: For example, removing a use-portion of extract can be a messy, and inconvenient process because the extract can be sticky and difficult to handle and often involves the use of small tools ("dab tools"). Furthermore, it is difficult, almost to the point of impossibility to accurately and repeatably acquire a consistent size portion of an extract. As a result, users may inadvertently under—or over dose themselves. This issue is particularly acute with concentrates because of their increased potency over flower material. Furthermore, for medical patients, the ability to have consistent dosing may be vital for a physician directed treatment regimen. Finally, the process for vaporizing extracts, particularly in precisely controlled electronic vaporizers, is problematic due to the difficulties of handling cannabis extracts, especially in inserting a portion of an extract into the vaporizing chamber of vaporizers.

SUMMARY

As specified in the Background Section above, there is a need in the art to develop improved dosage forms, packaging, and vaporization devices for vaporizable cannabis extract formulations. Therefore, this disclosure provides:

A portioned extract product comprising a vaporizable formulation that is separated into individual use portions and provided in a package wherein the individual use portions may be readily selected and removed by a user. In some cases the individual use portions are formulated such that each portion has a consistent ratio of active ingredients, and each portion provides a consistent dose or number of doses. In some embodiments, each portion is contained within the void of a mold tray. In some embodiments, each portion sits on top of a backing sheet. In some embodiments, each portion is associated with a structural matrix. Individual use portions may contain several doses. In some embodiments the extract formulation is substantially solid at room temperature. In some embodiments the extract formulation is substantially liquid at room temperature.

A process for making a package containing individual portions of a vaporizable formulation comprising the steps of: dispensing a defined quantity of an extract into or onto a shape defining deposition space. In some embodiments the process includes the creation of the extract adapted for use in the process. In some embodiments the process includes a curing step. In some embodiments, the deposition space is a mold. In some embodiments, the deposition space is a surface, which may further comprise deposition regions, and backing regions, and where, in some embodiments, the backing regions have a coating adapted to impose structure on the dispensed extract. In some embodiments, each portion will be associated with a structural matrix. In some embodiments the extract will be introduced into the structural matrix such that the extract is distributed throughout the structural matrix. In some embodiments the extract will be injected into the structural matrix. In some embodiments the extract is deposited on top of a structural matrix and then, may in some embodiments, be pressed into the structural matrix by rollers or other suitable process.

An applicator-tab embodiment including, for example, an applicator formed as a hand-graspable implement carrying a portioned extract product. In one embodiment the implement is a substrate material. In one embodiment, the applicator-tab is designed for vaporizer use with the user releasing the tab from the applicator and depositing the tab into the heating chamber. In other embodiment, the applicator is heat stable and the applicator and tab are together applied to a preheated vaporizer bowl.

An applicator-tab embodiment providing a pre-loaded, disposable/recyclable dab tool to facilitate vaporizer loading with a consistent/uniform dose of a vaporizable formulation. A packaged plurality of applicator-tab embodiments may be provided, for example, within a bottle or other container.

A vaporizer or operative portion thereof adapted for use with the portioned extract product. In particular, one embodiment having a preformed depression or cavity similarly shaped to the vaporizable formulation. The depression or cavity receiving the vaporizable formulation before or during use.

A system for providing precise doses and facilitating use of a portioned extract product comprising a supply of a portioned extract product and a vaporizer or operative portion thereof adapted for use with the portioned extract product.

These and other needs and disadvantages are overcome by the methods, systems, and compositions of matter disclosed herein. Additional improvements and advantages may be recognized by those of ordinary skill in the art upon study of the present disclosure.

BRIEF DESCRIPTION OF THE DRAWINGS

FIG. 6G depicts a cross-sectional view of vaporizer receiving an individual dose portion.

FIG. 10 illustrates another embodiment of the present invention with the RTSE provided in segmented units defining individual use dosages.

Figure 1A:
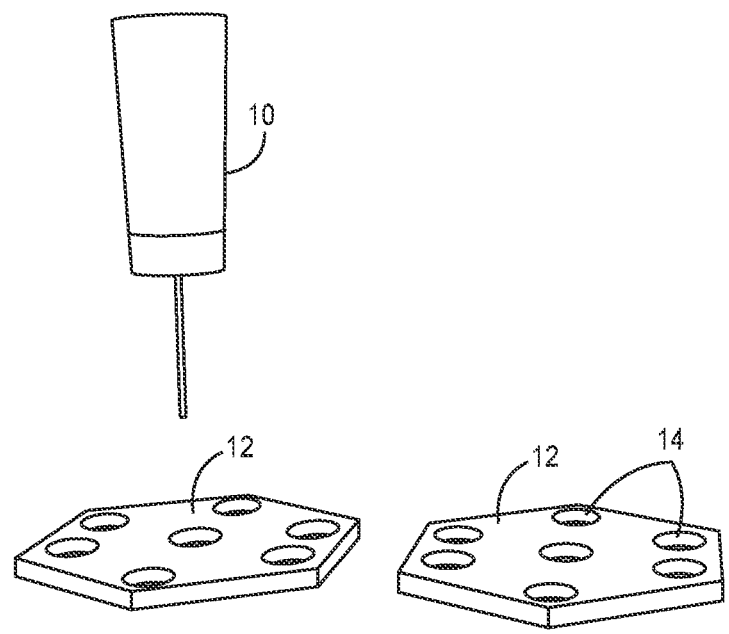
FIGS. 1A-1B illustrate processing techniques of forming an exemplary implementation of a single use vaporizable formulation in accordance with one embodiment of the present invention. 1A shows an example of a dispenser filling a mold tray with RTSE/precursor material and 1B shows an example of an overmold concept.

The Figures are exemplary only, and the implementations illustrated therein are selected to facilitate explanation. The number, position, relationship and dimensions of the elements shown in the Figures to form the various implementations described herein, as well as dimensions and dimensional proportions to conform to specific force, weight, strength, flow and similar requirements are explained herein or are understandable to a person of ordinary skill in the art upon study of this disclosure. Where used in the various Figures, the same numerals designate the same or similar elements.

DETAILED DESCRIPTION

These and other systems, methods, objects, features, and advantages of the present disclosure will be apparent to those skilled in the art from the following detailed description of the embodiments and drawings.

All documents mentioned herein are hereby incorporated in their entirety by reference. References to items in the singular should be understood to include items in the plural, and vice versa, unless explicitly stated otherwise or clear from the text. Grammatical conjunctions are intended to express any and all disjunctive and conjunctive combinations of conjoined clauses, sentences, words, and the like, unless otherwise stated or clear from context The cannabinoids are a class of molecules primarily obtained through the extraction of cannabis plant material, although synthetic and/or bioreactor production may also be used. The various cannabinoids include tetrahydrocannabinol (THC), cannabidiol (CBD), ("the major cannabinoids"), tetrahydrocannabinolic acid (THCA), Cannabidiolic acid (CBDA), cannabinol (CBN), cannabigerol (CBG), cannabichromene (CBC), tetrahydrocannabivarin (THCV), and cannabidivarin (CBDV) as well as others ("the minor cannabinoids"). Various cannabinoids, used alone or in combination have shown a variety of significant biological effects including but not limited to pain relief, anticancer, anti-inflammatory, antiemetic, anticonvulsant, and many others, including recreational effects.

Throughout this disclosure cannabis extracts are typically used to illustrate embodiments although any vaporizable formulation may be used wherein such extract formulations may include cannabinoid formulations, formulations comprising a mixture of cannabinoid and non-cannabinoid components, and exclusively non-cannabinoid components.

The Products: An embodiment is a portioned extract product comprising a cannabis extract that is separated into individual use portions and provided in a single package wherein the individual use portions may be readily selected and removed by a user. In some cases the individual use portions are formulated such that each portion has a consistent ratio of cannabinoids and/or terpenes, and each portion provides a consistent dose. In some embodiments, each portion is contained within the void of a mold tray. In some embodiments, each portion sits on a backing sheet. In some embodiments, each portion is associated with a structural matrix. In some embodiments the extract is substantially solid at room temperature. In some embodiments the extract is substantially liquid at room temperature.

Sizes of individual use portions may vary but portion sizes of about 5-25 mg; 25-50 mg; 50-75 mg; 75-100 mg, 100-200 mg, and 200-333 mg are specifically contemplated.

Generally cannabis extracts can be created using any methods known to those having skill in the art or later invented. Some examples of extraction methods suitable for use in forming extract for the portioned extract products include, but are not limited to, ethanol extraction, CO2 extraction, isopropanol extraction, "hydrocarbon" extraction: such as n-pentane, butane, propane and/or combinations thereof, and the like. In some embodiments, the extract will be carefully formulated to a defined chemical profile—consistent cannabinoid/terpene profile and consistent dosage and potency. In some embodiments, the extract will not be carefully formulated and the chemical makeup of the starting material will determine the final chemical profile of the extract. In some embodiments, the individual use portions contained in the portioned extract product are of a uniform size. In other embodiments the individual use portions are of varied sizes (ie X, 2X, 3X . . . NX). In some embodiments each individual use portion will have the same formulation. In other embodiments the individual use portions will be of varied formulations (e.g., a variety pack.)

In some embodiments the individual use portions will be formed by a molding process. While this can be done by any methods known to those having skill in the art, the following two methods are presented as suitable examples. The first method is an "overmold" process wherein a mold template ("overmold") is placed on a backing layer. Extract is then dispensed into voids of the overmold. After a sufficient time to settle, and/or cure, the overmold is removed leaving well-formed individual use portions.

In a second method extract is dispensed into voids in a mold tray. After sufficient settling and/or curing, a backing sheet is secured over the mold tray, sealing each individual dose portion into an isolated compartment. In other embodiments, a backing sheet can be placed over the mold tray and then the mold tray can be removed leaving well-formed individual dose portions disposed on the backing sheet which can then be sealed into a package.

In some embodiments the individual use portions will be dispensed directly onto a substrate or other surface, reminiscent of candy "dots" on wax paper.

FIG. 1 shows discrete individual use portions but in some embodiments, such as shown in FIG. 10, the extract will not be comprised of discrete portions. Instead, the extract will be formed into a single slab, wherein the slap further comprises "break" lines, e.g., indentations in the extract enabling a user to break off a single use portion of known dosage, reminiscent of a chocolate bar in which individual portions can be broken off. In such embodiments, extracts that are substantially solid at room temperature are preferable.

In some embodiments the extract will be associated with a structural matrix into which or onto which the extract is dispensed. In some embodiments the extract is infused into the structural matrix. The use of structural matrices will enable even easier handling of the extract insofar as the structural matrix provides additional structural. Structural matrices should be chemically inert and robustly thermostable. Examples of structural matrices include fritted glass, ceramic foam, perforated glass pieces, glass foam, glass or ceramic porous matrices, mineral based ceramic matrices, wire pads, hollow cylinders formed from wire mesh, and the like. In some embodiments, the structural matrices are reusable or recyclable. The structural matrices may take any shape, for example, spheres, discs, cylinders, cubes, hexagons, pentagons, octagons, and the like. In some embodiments the structural matrix may be created such that it will hold a defined dose/quantity of extract.

In some embodiments the individual use portions are provided in a package. In some embodiments multiple dosages and/or multiple formulations are provided in a single package. Products formed by Method Two above may be packaged like a blister pack, and placed into secondary packaging such as a box or sleeve. Perforations in the mold tray and backing are provided in some embodiments enabling the easy separation of individual use portions. In products wherein the individual use portions are disposed on top of a backing layer, a voided tray overlay may be placed and sealed over the individual dose portions. Perforations on the backing layer and overlay will provide easy separation of individual doses in some embodiments. In some embodiments, the backing sheet/surface will further comprise a visual design such that the deposited individual dose portions are integrated into the design, for example as spots on a leopard, suckers on an octopus tentacle, or any other design dreamed into existence by creative minds.

The Process: Another embodiment is a process for making individual-use portions of a cannabis extract ("portioned extract product") comprising the steps of: dispensing a defined quantity of an RTSE into a deposition space. In some embodiments the process includes the formulation of a cannabis extract or suitable precursor adapted for use in the process. In some embodiments the process includes a curing step. In some embodiments, the deposition space is a mold. In some embodiments, the deposition space is a surface, which may further comprise deposition regions, and backing regions, and where, in some embodiments, the backing regions have a coating adapted to impose structure on the dispensed extract. In some embodiments, each portion will be associated with a structural matrix. In some embodiments the extract is infused into the structural matrix. In some embodiments the extract will be injected into the structural matrix. In some embodiments the extract is deposited on top of a structural matrix and then, may in some embodiments, be pressed into the structural matrix by rollers or other suitable process. In some embodiments the extract or extract precursor is heated to facilitate infusion into the structural matrix. In some embodiments the infusion process is facilitated by vacuum.

Generally speaking the first step in the process is to obtain a cannabis extract and prepare it for dispensing into the deposition space. Extract can be obtained commercially from grower-processors or created on an as-needed basis. Generally cannabis extract can be created using any methods known to those having skill in the art or later invented. Of particular interest are extracts that are formed using solvents that readily evaporate out of the created extracts at commercially reasonable temperatures and pressures. Some examples of extraction methods suitable for use in forming extract for the portioned extract product include, but are not limited to, ethanol extraction, CO2 extraction, isopropanol extraction, "hydrocarbon" extraction: such as n-pentane, butane, propane and/or combinations thereof, and the like. Post-extraction processes may be used on the extract to alter its appearance and/or structural characteristics, such as filtration steps, whipping, mixing, aerating, and the like. Post extraction processes are generally known by those in the art for making budders, waxes, honeycomb, and the like.

In some cases, no preparation will be required prior to dispensing. Because of the solid/semisolid nature of the extract, in order to dispense an unprepared extract, special equipment used for dispensing pastes or other semisolid preparations will likely be required. With respect to preparing the extract for dispensing, this may be done by heating the extract in order to make it less viscous and easier to dispense. Furthermore, extract precursor solution may be prepared and used to facilitate dispensing. "Precursor solution" is a solution of cannabis extract that is solvent enriched. This may be obtained by adding solvent back into an extract or by limiting the purging process associated with a solvent extraction while a significant amount of solvent remains. The exact amounts of solvent that should be present in a precursor solution are dependent on a variety of variables such as: desired viscosity, time needed to cure the resulting product, desired rolling of the curing process, desired characteristics of the final product, and the like.

Another preparatory step that may be used in some embodiments is formulation of the extract and/or precursor solution. Formulation steps are used when a precise formulation is desired. Precise formulations include, defined ratios of THC:CBD, precise amounts of cannabinoids, defined ratios of total cannabinoids to terpenes, defined ratios of major to minor cannabinoids, and the like. Furthermore, the total cannabinoid content may be modified in some embodiments, to ensure that each individual use portion has a consistent dose profile, ie the same amount of cannabinoids. In some embodiments the amount of cannabinoids are controlled by altering the amount of extract formulation dispensed. Additional formulation steps are those adapted to modify the structural characteristics of the extract which may be used alone or in combination with other formulation activities. Formulation steps adapted to modify the structural characteristics of the extract include but are not limited to the addition of vaporizer safe additives that induce a more rigid (solid) structure. For example, crystalline THCA and/or crystalline CBD and/or CBDA, or other crystalline cannabinoids.

The next step in the process is dispensing the extract/precursor solution into a deposition space. This can be done with any methods known to those having skill in the art. Some methods may be as simple as manually pipetting the extract into the deposition space. More efficient, automated methods may be preferable. Automated dispensing methods include automated dispensing pens, multichannel dispensing apparatus, and the like. In an embodiment the dispensing is done with a multichannel dispensing pen wherein each output of the multichannel dispensing apparatus corresponds to a deposition site. Using such a setup, the entirety of a package can be deposited in a single deposition cycle. In some embodiments, a device substantially similar to a 3D printing head may be employed to precisely dispense a fixed amount of extract/precursor into a specified deposition site. In some embodiments a dispensing device capable of maintaining increased pressures is utilized to dispense precursor solutions wherein the solvent used is a gas at room temperature and 1 atm.

Generally speaking, the extract/precursor will be dispensed into a mold or onto a surface. As more fully described above overmolds or mold trays may be used. Regardless of the specific methods, the molds are shaped to impart a shape on the final individual dose portions. There is no practical limit to the amount of different shapes that can be used. Simple shapes such as triangle, squares, rectangles, squares, pentagons, hexagons, septagons, octogons, and the like may be used. More fanciful shapes such as hearts, flowers, leaves, and the like, may also be used. 2D and 3D shapes are specifically contemplated. In a specific embodiment, the shape used is a multi-faceted geometric shape similar to a cut jewel.

Because the cannabis extract tends toward stickiness, any surfaces that come in contact with the extract may benefit from being adapted to be non-stick. Such surfaces may be on molds, and/or backing layers/sheets. Nonstick surfaces may be parchment paper, non-stick coatings such as PTFE, oleophobic coatings, and the like. Specifically, contemplated are hemp based "papers" that have been "parchmentized" by exposure to acid—in a method known to those having skill in the art.

One of the benefits of this process is to produce individual dose portions of uniform size. Uniform size may be accomplished by dispensing a known mass or volume of extract/precursor. Another way to achieve uniform size is to use a mold with a known, fixed volume and fill each mold consistently. In some embodiments, this may further comprise overfilling the molds and scraping the excess off, leaving a fixed volume behind. The scraping step may be done with a heated blade to facilitate easy removal and to form a clean, smooth, surface on the remaining individual dose portions. In another embodiment, rollers or other suitable tamping devices may be used to press down any extract that has risen above the border of the mold. This embodiment has the added characteristic of enabling dispensing by mass and may ensure more consistent dose.

In other embodiments, the extract/precursor is dispensed onto a surface, instead of into a mold. In some embodiments, the surface has been adapted to provide structure to the deposited extract. In an embodiment the surface comprises a coating tending the make the deposited extract "bead" up. Examples of such surfaces include oleophobic surfaces and/or PTFE coated surfaces. In some cases, a hydrophobic surface may be used depending on the water content of the extract. In some embodiments the surface comprises deposition sites and background surface wherein the background surface is more oleophobic than the deposition sites such that the deposited extract will spread out to the limit of the deposition site surface and "bead" up along the boundary of the deposition site surface and the background surface thereby imposing structure on the deposited extract material.

In embodiments where the deposited extract is associated with a structural matrix as described above, the extract may be deposited in to, on to, or on to and pressed into the structural matrix. The "pressing in to" may be accomplished with rollers or other suitable commercial pressing method known to those having skill in the art.

Following dispensing into deposition spaces, a vibration step may be utilized in some embodiments to facilitate settling of the material.

In some embodiments the process includes a curing step or steps. The curing process may be as simple as allowing the dispensed material to sit at room temperature for a fixed interval. More complex curing methods are also contemplated. There is no practical limit on the variation of final product consistency/structural characteristics that can be created through variation of the solvent used and curing conditions. For example, dynamic alteration of atmospheric pressures and temperatures used during the curing process can be used to tune the structural characteristics of the final product. Furthermore, the nature of the remaining solvent used to make the extract as well as the amount and type of the solvent(s) remaining in the extract/precursor will have significant impact on the type of curing process used, and the ultimate structural characteristics of the final product. Generally speaking increasing temperature and decreasing atmospheric pressure will speed the purging/evaporation of the remaining solvent in the extract. Generally speaking temperatures should be kept below the temperatures at which the acid forms of cannabinoids decarboxylate, and the temperatures at which terpene, terpenoid, and flavonoid compounds readily evaporate. In a specific embodiment, using a hydrocarbon solvent, a low temperature and modestly decreased atmospheric pressure condition is used until the residual solvent levels reach about 0.1-2% at which point the atmospheric pressure suddenly and substantially decreased causing the formation of many small bubbles in the deposited RTSE. Following the decrease, the pressure can then be increased (but still less than 1 atm) until the remaining solvent is purged. In some cases, such as when solvents are used that are gases at room temperature, increased pressures may be used to slow the purging of the solvent.

After curing, the individual dose portions may be packaged in a primary packaging unit. In embodiments where the individual dose portions are on top of a surface (not within a mold void) a molded protective cover sheet can be placed over the individual dose portions and then sealed in place. In embodiments where the individual dose portions remain inside mold voids, a backing sheet is sealed over the exposed side of the mold, similar to blister packaging. In some embodiments an inert or preserving gas is introduced to the mold space to preserve the doses. In some cases the sealing is done under elevated pressure to provide additional structural stability to the package and protect the individual dosages. In some embodiments the primary packaging unit is child resistant. In some embodiments, the primary packaging unit is then placed into secondary packaging such as a box, sleeve, dispenser, or the like. The secondary packaging may be child resistant in some embodiments. In some embodiments the secondary packaging may further comprise a tool for extracting an individual dose portion. Primary packaging units and/or secondary packaging may further comprise fanciful designs and/or branding elements.

The vaporizer: Another embodiment is a vaporizer, or operative part thereof, adapted for use with individual dose portions of an RTSE.

Generally speaking the vaporizer is a device having a heating chamber that vaporizes an active ingredient. In some embodiments a cup made from a suitable material is within the heating chamber. A mouthpiece reversibly engages with the vaporizer. The mouthpiece further comprises a removable dosing tool, which may, in some embodiments be reversibly coupled to the mouthpiece, and adapted to engage with single doses of extract from a package. For example, the dosing tool has a flattened engager such as those shown in the examples. The engager of the dosing tool may be shaped to correspond to the specific shape of individual dose portions. For example, a hexagon engager to be used with hexagon extract dose portions.

The bottom of the cup has an indentation adapted to accept a single dose of an extract. Adaptations may include being shaped to match the shape of individual doses of extract. The bottom of the chamber with the indentation, in some embodiments, is made of a porous material such as ceramic foam, fritted glass, or the like. The chamber and mouthpiece are configured such that when the mouthpiece is placed on the vaporizer the dosing tool disposes an individual dose of extract into the indentation.

An embodiment is a vaporizer further comprising a heating chamber adapted for vaporizing at least one active ingredient; wherein the heating chamber further comprising walls and a floor, and the floor having an indentation wherein the shape of the indentation corresponds to the shape of an individual dose portion of an extract.

The System: Another embodiment is a system, in some cases provided as a kit, for providing precise doses and facilitating use of a portioned extract product comprising a supply of a portioned extract product and a vaporizer or operative portion thereof adapted for use with the portioned extract product.

Figure 1B:
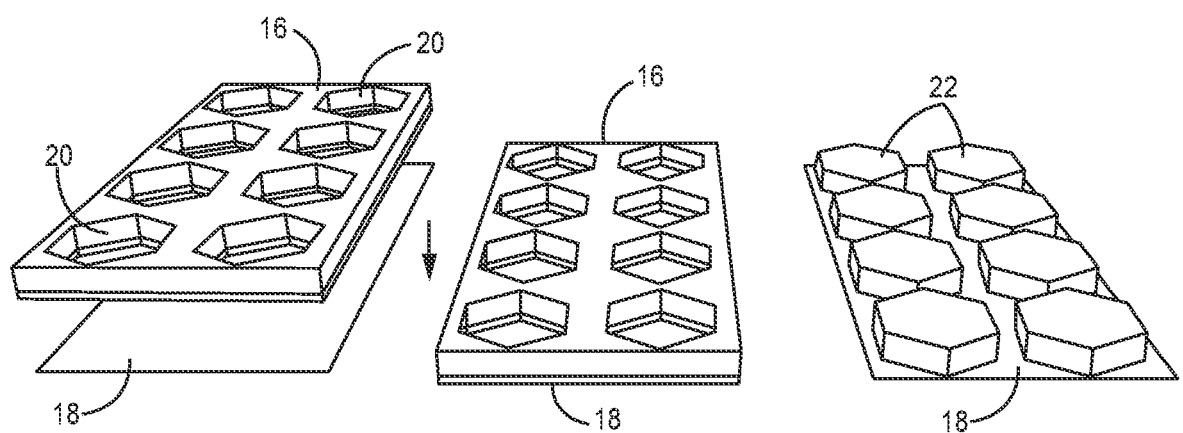

Now, with reference to the figures:

FIG. 1A top shows an example of a dispenser 10 filling a mold tray 12 with RTSE/precursor material to define individual dose portions 14. FIG. 1B shows an example of an overmold concept, wherein a mold 16 and mold sheet 18 create a plurality of shaped voids 20, into which RTSE/precursor is dispensed. After curing the mold 16 is removed leaving behind well-formed individual dose portions 22 upon mold sheet 18.

Figure 2A:
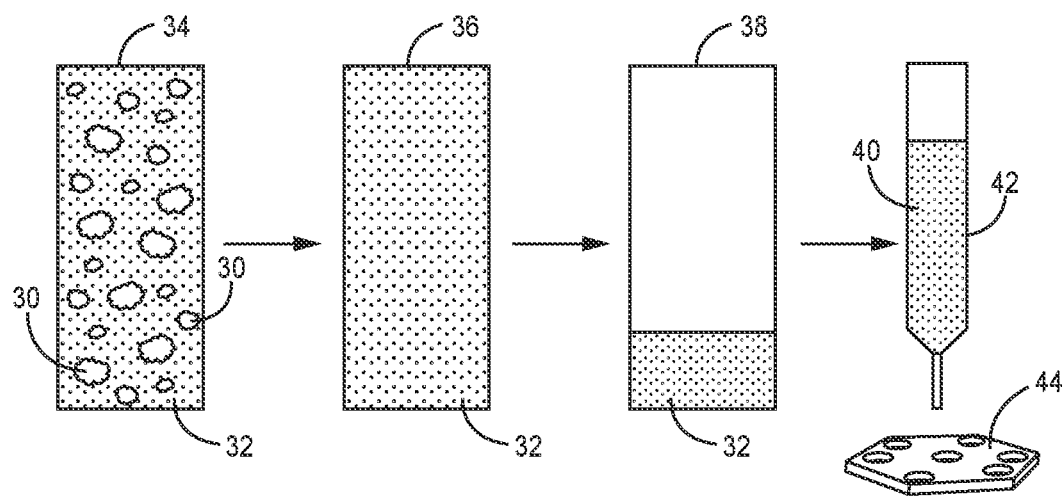
FIGS. 2A-2C illustrate additional processing techniques of forming exemplary implementations of single use vaporizable formulations in accordance with other embodiments of the present invention. 2A shows a process for preparing a precursor solution, which is loaded into a dispensing device, for deposition into a mold; 2B shows a curing step for the deposited precursor solution; and 2C shows deposition and curing of the precursor solution in a structural matrix.

FIG. 2A generally illustrates the process for creating individual dose vaporization formulations using a precursor solution. FIG. 2A shows a solvent extraction in which cannabis material 30 is exposed to solvent 32 at step 34, then filtered to remove particulate matter at step 36, then most of the solvent 32 is evaporated off at step 38, but leaving enough solvent to make the solution easy to work with, but more solvent than would be appropriate for a final vaporizable product, thereby forming a precursor solution 40. The precursor solution 40 is then loaded into a dispensing device 42 for dispensing into a deposition space, such as mold 44, as described herein.

Figure 2B:
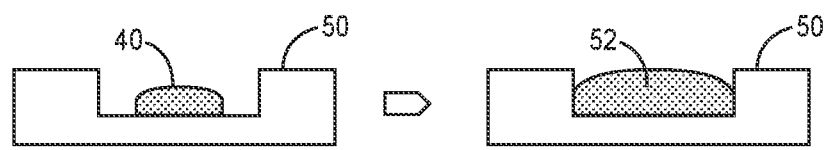
Figure 2C:
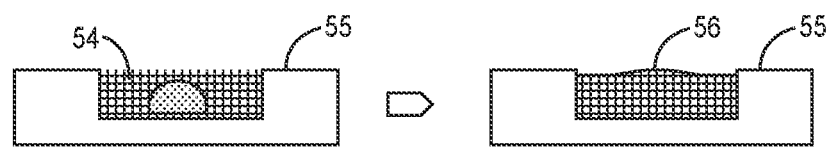

FIG. 2B illustrates a curing step, in this case depicted in a mold 50, wherein the deposited precursor solution 40 is exposed to atmospheric pressures sufficient to purge the solvent from the precursor at a desired rate to yield an individual dose portion 52. In some cases temperatures will also be elevated during the curing step. FIG. 2C illustrates the precursor solution 40 being deposited in carrier 55 and cured in a structural matrix 54 to yield another embodiment of individual dose portion 56.

Figure 3A:
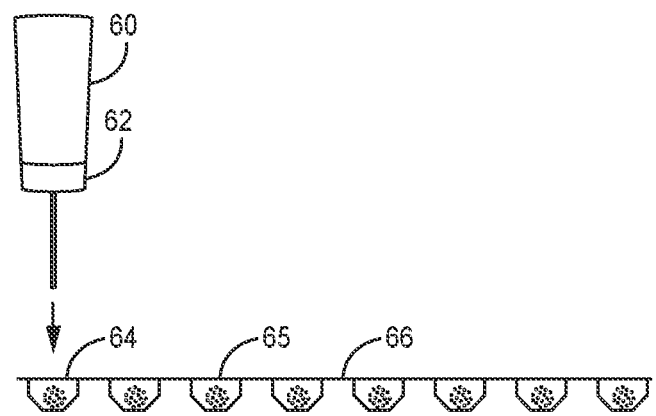
FIGS. 3A through 3D illustrate processes for dispensing RTSE/precursor into the void cavities of a mold tray and creating a primary unit of individual doses according to yet another embodiment of the present invention. 3A illustrates a dispensing pen for dispensing the RTSE/precursor; 3B illustrates a curing step for the dispensed RTSE formulation; 3C illustrates application of a backing sheet to the mold; and 3D illustrates removal of the mold to provide a sheet of individual RTSE doses.
Figure 3B:
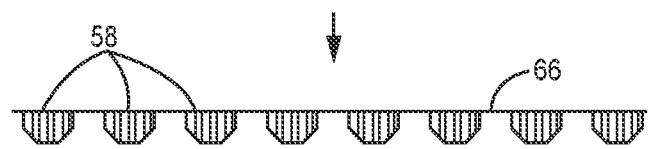
Figure 3C:
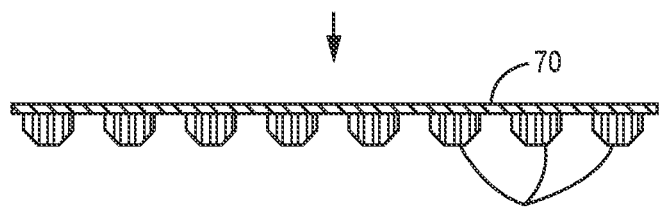
Figure 3D:
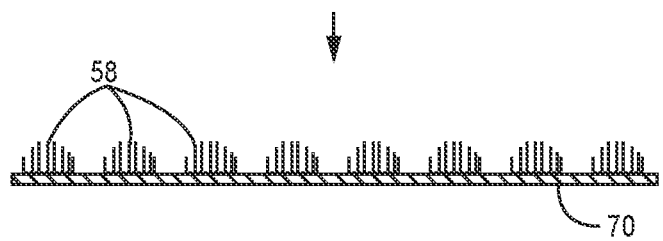

FIG. 3A through 3D illustrate processes for dispensing RTSE/precursor into the void cavities of a mold tray and creating a primary unit of individual doses 58. In FIG. 3A, a dispensing pen 60 dispenses a defined quantity of RTSE/precursor 62 into the void cavities 64 of a mold 66. In this embodiment, void cavities 64 include a structural matrix 65. In other embodiments, void cavities 64 are initially empty. FIG. 3B represents a curing step where solvent is evaporated from the RTSE/precursor formulation. The apparent increase in volume in the RTSE formulation between FIGS. 3A and 3B illustrates the ability of a curing step to alter the structural characteristics, in this case by capturing a plurality of bubbles within the RTSE/precursor, thereby expanding it to individual doses 58. FIG. 3C represents the application of a backing sheet 70 to the mold-RTSE complex. In some embodiments, the backing sheet 70 may be fused to the mold tray 66, in which case the complex of mold tray 66 and backing sheet 70 could be further packaged as ready for sale. In some cases, such as illustrated in FIG. 3D the mold tray 66 can be removed leaving a sheet of individual RTSE doses 58 which can then be further packaged for sale.

Figure 4A:
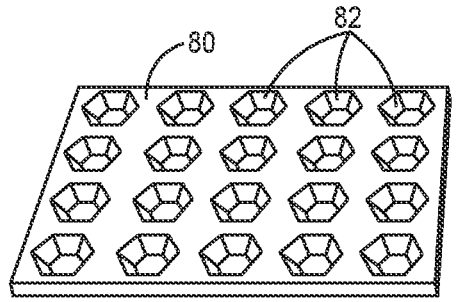
FIGS. 4A through 4F illustrate processes for dispensing RTSE/precursor into the void cavities of a mold tray and creating a primary units of individual doses according to yet another embodiment of the present invention. 4A illustrates a mold tray having geometrically-shaped cavities; 4B shows exemplary individual dose portions on a backing layer; 4C shows application of a protective top layer to the dose portions; 4E shows a filled mold try with sealed individual use portions; and 4F illustrates a process for packaging individual dose portions.
Figure 4B:
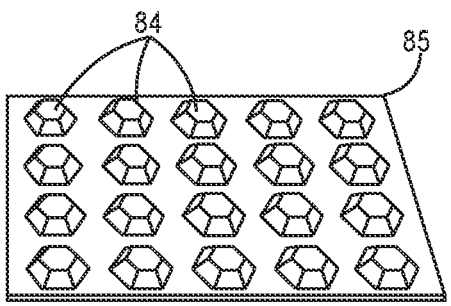
Figure 4C:
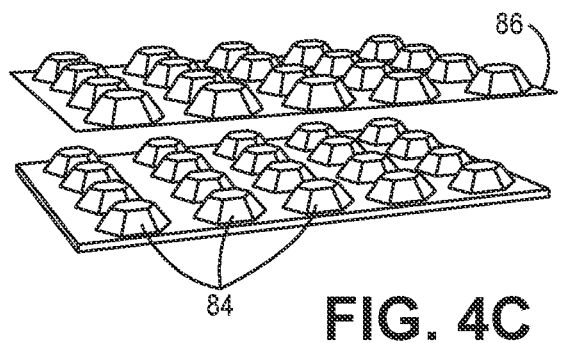
Figure 4D:
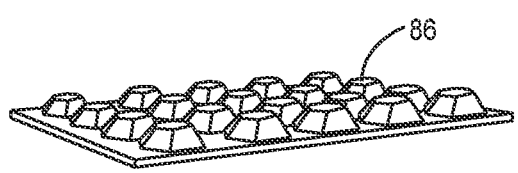
Figure 4E:
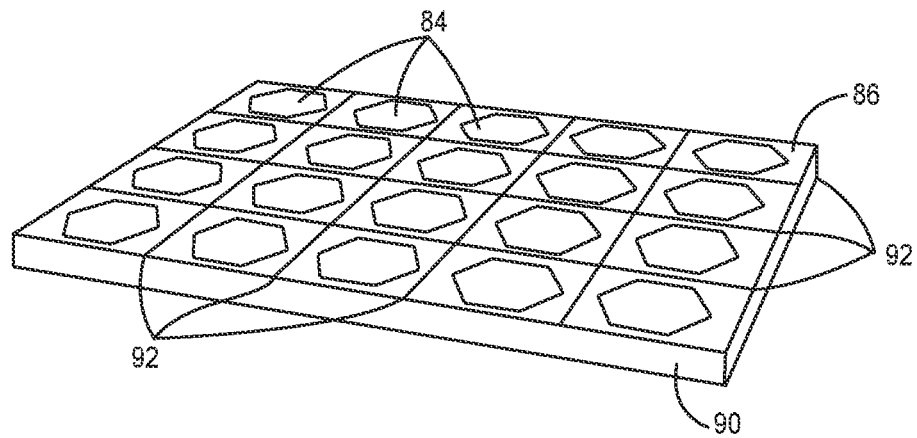

FIGS. 4A through 4E shows an embodiment where the shape of the individual dose portions take on the characteristic faceted shape of a jewel as well as different methods of processing. FIG. 4A is an example of a mold tray 80 defining a plurality of geometric shape cavities 82. FIG. 4B shows an example of individual dose portions 84 disposed on a backing layer 85 having taken on the characteristic shape of the cavities 82 of mold tray 80. FIG. 4C shows the application of a protective top layer 86 being applied over a sheet of individual use portions 84 where it can secured in place as shown in FIG. 4D. FIG. 4E shows a filled mold tray 90 in which the individual use portions have been sealed. Panel E also illustrates examples of perforations 92 facilitating the easy removal of individual dose portions 84.

Figure 4F:
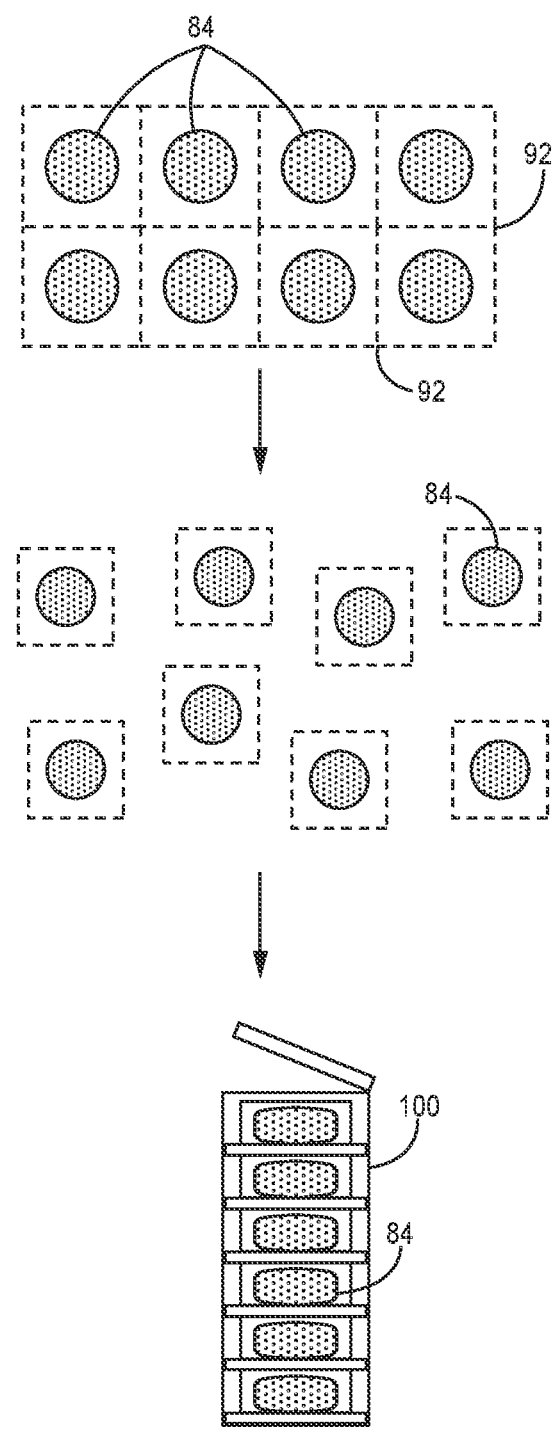

FIG. 4F shows one example of how the individual dose portions 84 may be packaged. In this case, the individual dose portions 84 having been separated from each other are placed in a secondary package, such as child resistant container 100.

Figure 5A:
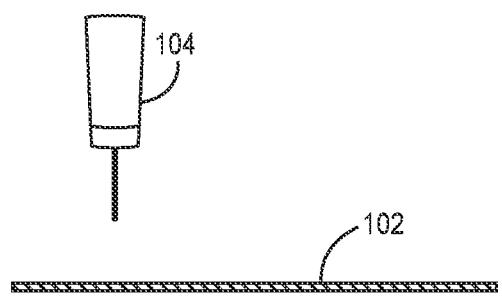
FIGS. 5A-5E illustrate processes and dispensing approaches in accordance with yet another embodiment of the present invention. 5A depicts the deposition of RTSE/precursor onto a surface via dispenser; 5B illustrates the concept of deposition zones and background zones; 5C illustrates a curing process in which a plurality of bubbles is introduced to the RTSE; 5D illustrates the incorporation of design elements into the process, showing individual, round, dose portions forming the spots of a leopard; and 5E shows another example of a package form wherein different formulations are provided in a single package.
Figure 5B:
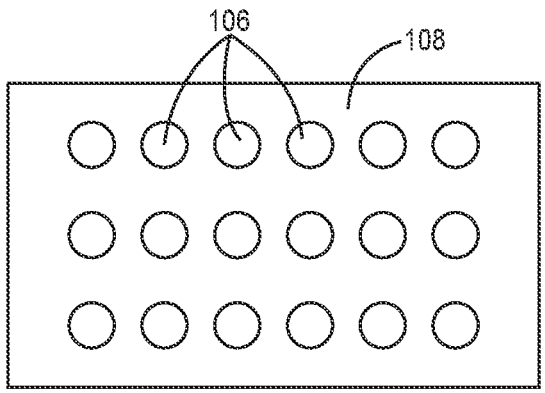
Figure 5C:
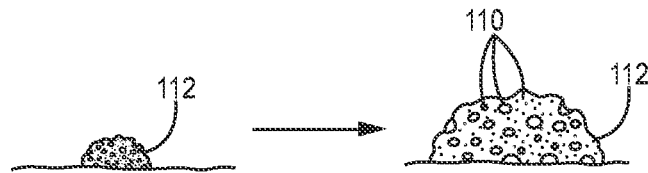
Figure 5D:
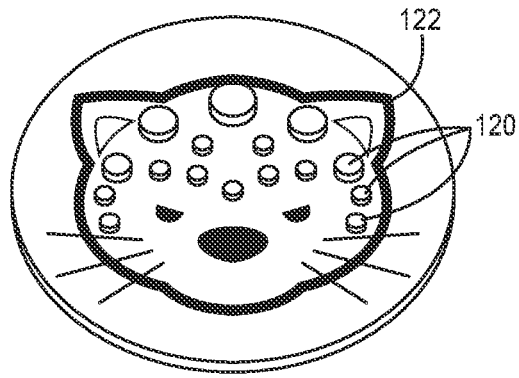
Figure 5E:
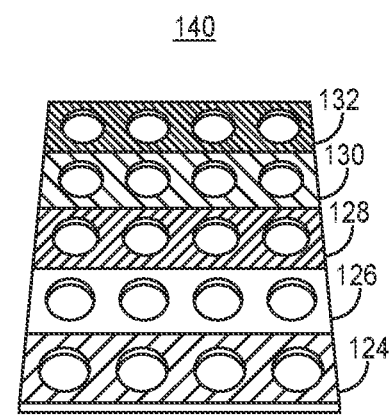

FIG. 5A depicts the deposition of RTSE/precursor onto a surface 102 via dispenser 104. FIG. 5B illustrates the concept of deposition zones 106 and background zones 108. Further illustrated here is the use, in some embodiments, of labeling on the deposition zones. Insofar as some RTSE is essentially transparent, labeling, branding, or other design elements may be visible through the RTSE. FIG. 5C illustrates a curing process in which a plurality of bubbles 110 is introduced to the RTSE 112 by dynamically altering temperature and/or pressure during the curing process. FIG. 5D illustrates the incorporation of design elements into the process. In this example individual, round, dose portions 120 have been integrated into a design 122 to form the spots of a leopard. Note also that different dose portion 120 sizes are provided within a single package/design. The design, in some embodiments, is used as an indicator to communicate to users the characteristics of the individual doses, such as formulation, potency, and the like. FIG. 5E shows another example of a package form wherein different formulations 124, 126, 128, 130, 132 are provided in a single package 140. In this case different colors, patterns or other indicia are being used to communicate the ratio of THC to CBD in the individual dose portions with different formulations 124, 126, 128, 130, 132.

Figures 6A, 6B:
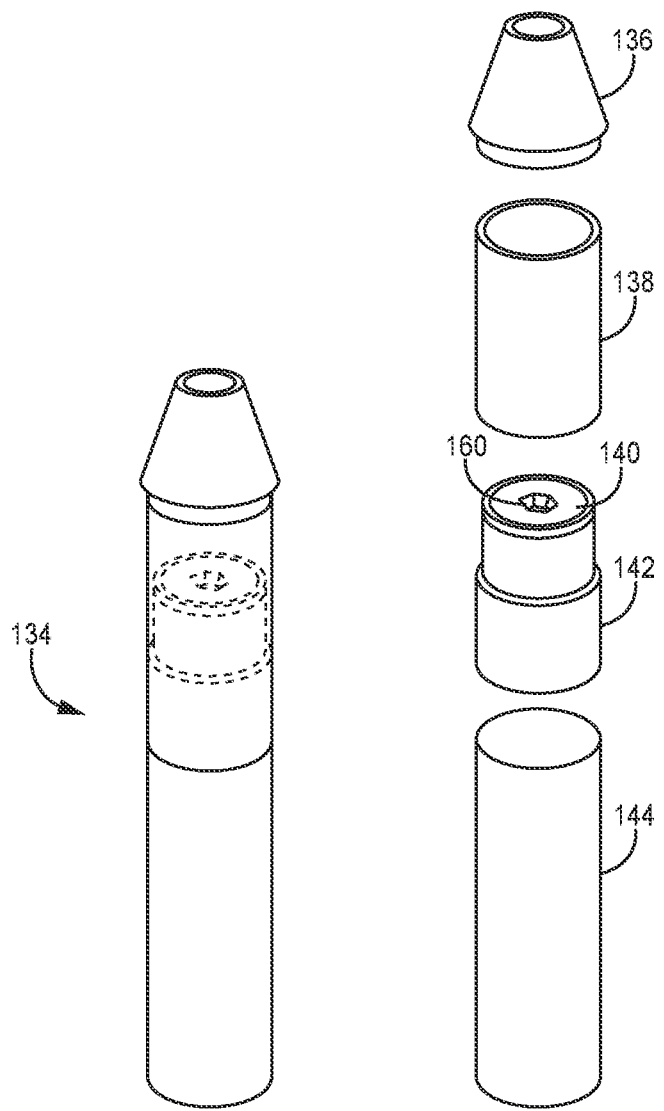
FIGS. 6A and 6B illustrate a vaporizer device in accordance with an embodiment of the present invention.

FIG. 6A illustrates a vaporizer device 134 adapted for use with an individual dose portion of the present invention. Additional details of vaporizers are disclosed in US Patent Application Publications US2017/0295845A1 and US 2018/0000161A1, both being incorporated herein by this reference. FIG. 6B illustrates the vaporizer device 134 components, including a mouthpiece portion 136, heating chamber 138, heating chamber floor 140, heating element 142 and power supply 144.

Figure 6C:
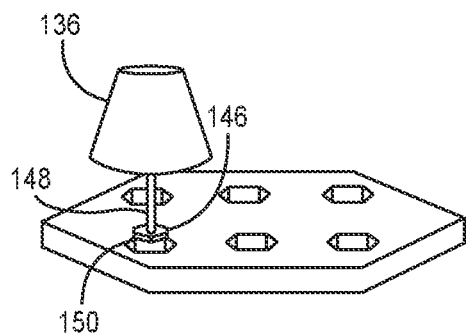
FIGS. 6C-6G illustrate detailed portions and use of a vaporizer of FIG. 6A in accordance with the present invention. 6C shows the operative portion of the vaporizer showing an attachment of an individual dose portion. The mouthpiece and dose are returned to the vaporizer as shown in FIGS. 6D and 6E. The mouthpiece is reengaged with the vaporizer as shown in FIG. 6F.
Figure 6D:
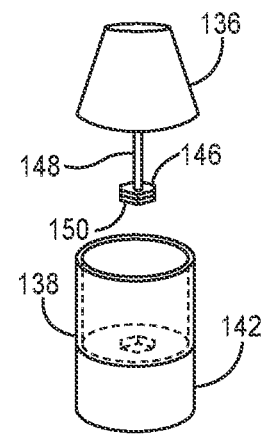
Figure 6E:
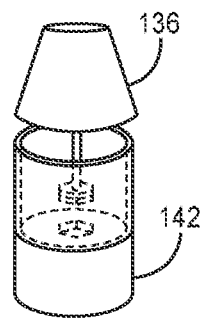
Figure 6F:
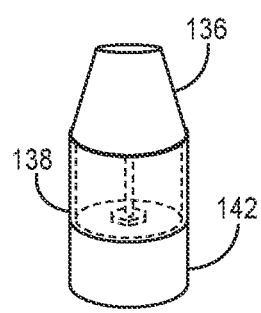
Figure 6G:
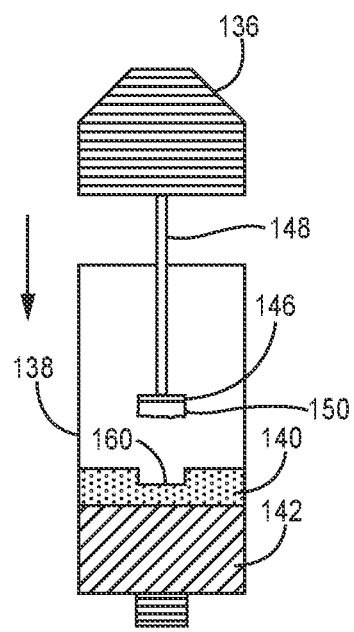

FIGS. 6C through 6F shows how the operative portion of a vaporizer device 134 integrates with the products described herein to facilitate easy use of the individual use portions. In FIG. 6C, an engaging portion 146 at a terminal end of a dosing tool 148, reversibly coupled to the mouthpiece portion 136, is pressed into an individual dose portion 150 causing the dose 150 to attach to the engaging portion 146. The mouthpiece 136 and dose 150 are returned to the vaporizer 134 as shown in FIGS. 6D and 6E. The mouthpiece 136 is reengaged with the vaporizer 134 as shown in FIG. 6F. In so doing, the individual dose portion 150, attached to the engaging portion 146 of the dosing tool 148, is positioned in an indentation or hollow 160 inside the floor 140 of the heating chamber 138. FIG. 6G depicts a cross-sectional view of vaporizer 134 receiving an individual dose portion 150 attached to the engaging portion 146 of the dosing tool 148 attached to the mouthpiece portion. The dose portion 150 is deposited into the indentation 160 in the floor 140 of the heating chamber 138. In one embodiment an indentation or cavity is similarly shaped and sized to the vaporizable formulation.

Figure 6H:
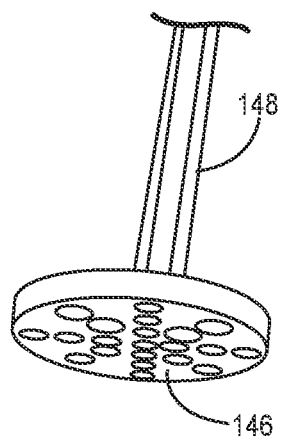
FIGS. 6H, 6I, and 6J illustrate three different configurations of a detailed portion of a dab tool, respectively, in accordance with the present invention.
Figure 6I:
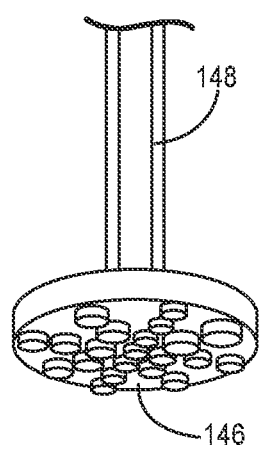
Figure 6J:
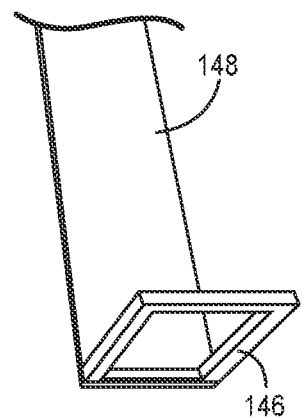

FIGS. 6H through 6J illustrate different examples of engaging portions 146 of the dosing tools 148.

Figure 7:
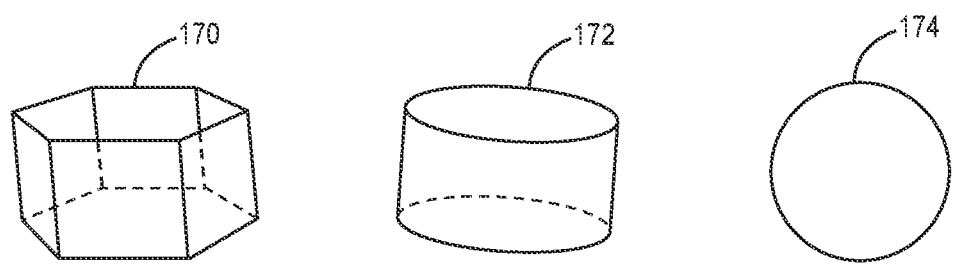
FIG. 7 illustrates embodiments of a structural matrix for use in accordance with the present invention.

FIG. 7 illustrates non-limiting examples of structural matrices suitable for use in RTSE/precursor processing. The structural matrix may include a geometric form, such as a hexagonal prism 170, a cylinder 172 or sphere 174. The spherical structural matrix 174 may be particularly useful as this form allows the matrix to roll around within the heating chamber which may aid in the release of the vaporization formulation contained within.

In some embodiments, the vaporization formulation is heated before dispensing into the structural matrix. In other embodiments, the structural matrix may also be heated before receiving the formulation. In yet another embodiment, both the structural matrix and the vaporization formulation are heated prior to combination.

In some embodiments, the matrix containing the formulation will be cured at decreasing temperatures. In some embodiments, the matrix containing the formulation will be cured at decreasing atmospheric pressure. The formulation may be a precursor solution as described above and containing an elevated solvent level, and the infused matrix will undergo a curing step to purge excess solvent from the matrix-formulation combination.

Figure 8A:
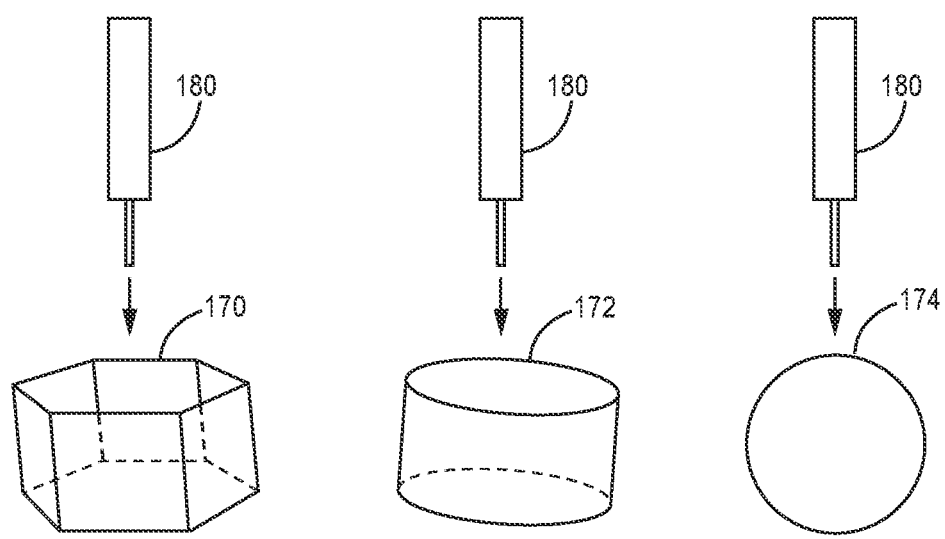
FIG. 8A-8C illustrate methods of infusing structural matrices with a vaporizable formulation in accordance with the present invention. 8A depicts one approach for infusing structural matrices of different geometries with a vaporization formulation; 8B depicts another approach to infusing a structural matrix with a vaporization formulation via injection; and 8C depicts another approach to infusing a structural matrix with a vaporization formulation by placing a matrix on top of a dispensed formulation.
Figure 8B:
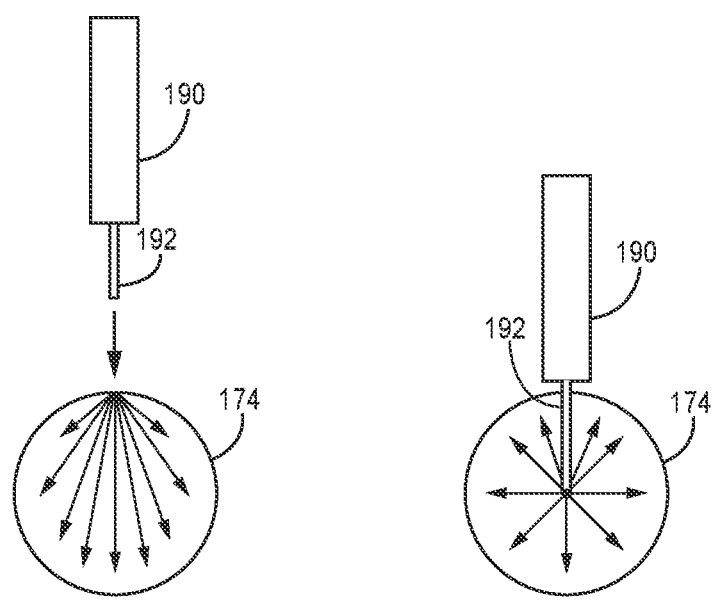
Figure 8C:
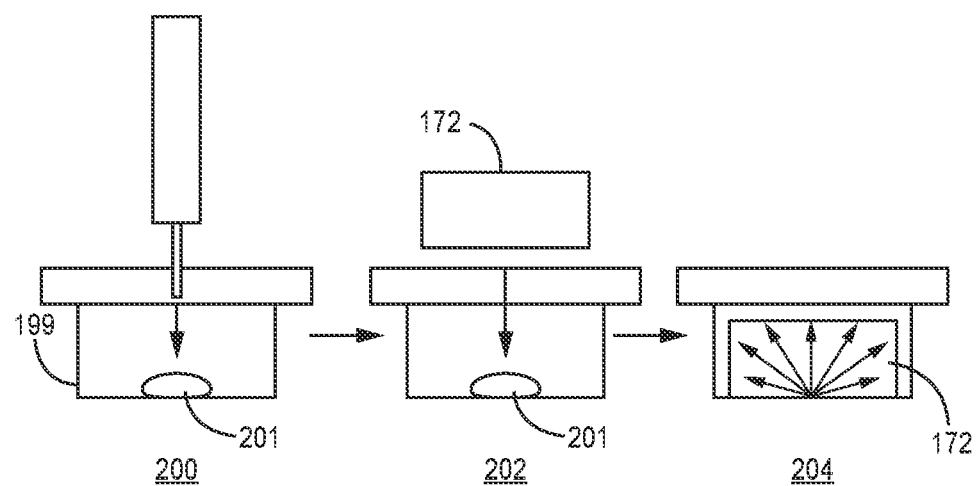

FIGS. 8A-8C illustrate examples of structural matrices and methods for associating matrices with RTSE/precursor. For example, RTSE/precursor can be injected into and/or deposited onto matrices. In some cases, RTSE/precursor is dispensed into a deposition site and a structural matrix is placed on top of the dispensed RTSE/precursor.

FIG. 8A depicts one approach for infusing structural matrices 170, 172, 174 with a vaporization formulation. As shown, a formulation is dispensed from a dispensing tool 180 positioned above the matrices 170, 172, 174 and a desired quantity of formulation is dispensed onto the matrix and allowed to infuse throughout the matrix. Infusion can also be done with matrices already placed in packaging, such as a blister pack.

FIG. 8B depicts another approach to infusing a structural matrix 174 with a vaporization formulation. As shown, a formulation is dispensed from a dispensing tool 190 having a syringe portion 192 which enters the structural matrix 174 to inject the formulation. In such an embodiment, a channel (not shown) may be needed to allow the syringe portion 192 to enter the matrix 174.

FIG. 8C depicts another approach to infusing a structural matrix 172 with a vaporization formulation. As a first step a desired quality of formulation 201 is deposited on a surface 199 depicted as step 200. Next the matrix 172 is placed on top of the dispensed formulation 201 at step 202 and the formulation is then allowed to disperse within the matrix 172 at step 204.

In one embodiment, a structural matrix 170, 172, 174 include one or more cavities for receiving the vaporizable formulation. For example, one or more open or closed-ended cavities can be included within the structural matrix 170, 172, 174. The one or more cavities can capture a predetermined volume of vaporizable material to provide consistent/uniform dosages. In one embodiment the structural matrix 170, 172, 174 is formed of non-porous material, such as glass or ceramic, with the one or more cavities defining the volume of vaporizable material delivered with each element.

Figure 9A:
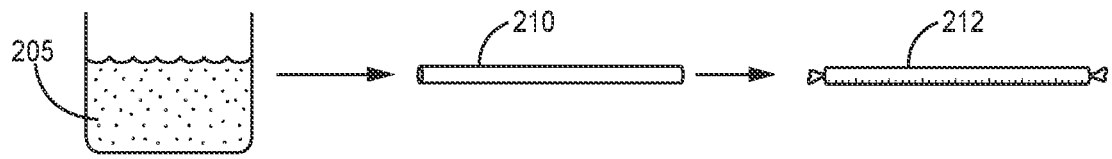
FIGS. 9A-9C illustrate other embodiments of the present invention with the RTSE provided in roll-form and dispensing techniques. 9A depicts a process of forming the RTSE into an elongated roll; 9B depicts the RTSE roll with defined divisions to facilitate consistent dosing; and 9C depicts the RTSE roll within a package (left), wherein the roll can be pushed out of the package by engaging with a push-out mechanism (right).
Figure 9B:
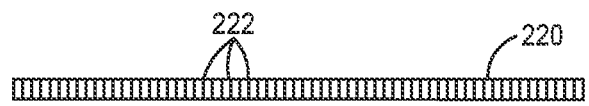
Figure 9C:
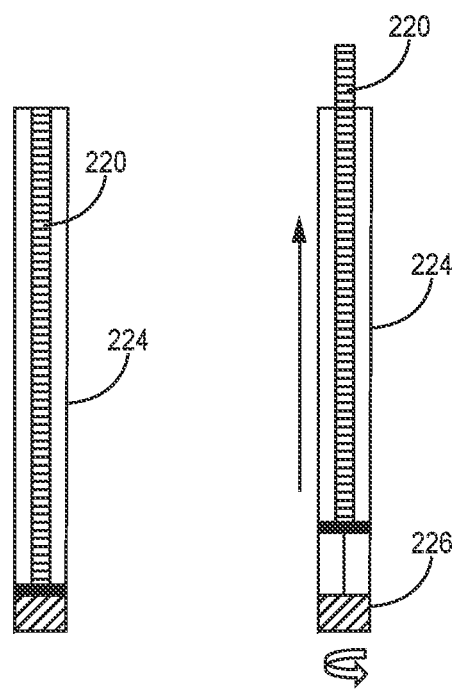

FIG. 9A shows a product and method for forming a package of RTSE 205 comprising forming the RTSE, using methods known in the art such as extrusion or rolling, into an elongated roll 210. The roll 210 may then be wrapped, for example, with a wrapper 212 having graduated indicia printed thereupon. While the term "roll" is used, this is should not be interpreted to mean the roll is round. Any cross sectional shape may be used, such as triangle, hexagon, and the like. The specific dimensions of the roll, in some embodiments are selected to provide a defined dosage per unit length of the roll—such as, for example, 25 mg every 5 mm, although the specific dosages per unit length can be varied. In one embodiment, the wrapper 212 further comprises demarcation notation to indicate the dosage contained per unit length of the roll, such as, for example, N-mg per division. The wrapper 212 may be a parchment paper or suitable equivalent. In other embodiments, wrapper 212 may be a casing. The wrapper 212 or casing may be impregnated with terpenes or other suitable chemicals to provide enhanced flavor characteristics to the RTSE. The surface of the wrapper 212/casing in contact with the RTSE will be a surface adapted for ready release of the RTSE (nonstick.) In one embodiment, as depicted in FIG. 9B, a roll 220 of RTSE includes defined divisions 222 to facilitate consistent dosing. FIG. 9C illustrates another embodiment where a roll of RTSE 220 is disposed within a package 224 wherein the roll of RTSE 220 can be pushed out of the package by engaging with a push-out mechanism 226. Containers with push-out mechanisms are known to those having skill in the art and can be readily adapted for this purpose.

An applicator-tab embodiment including, for example, an applicator formed as a hand-graspable substrate carrying a portioned extract product. In one embodiment, the applicator-tab is designed for vaporizer use with the user releasing the tab from the applicator and depositing the tab into the heating chamber. In other embodiment, the applicator is heat stable and the applicator and tab are together applied to a preheated vaporizer bowl.

FIG. 10 illustrates another example of an elongated roll-form RTSE 230 having predefined divisions 232 between segments of RTSE. The divisions 232 allow a user to break off and consume one or more uniformly sized units to provide consistent or uniform dosing.

Figure 11A:
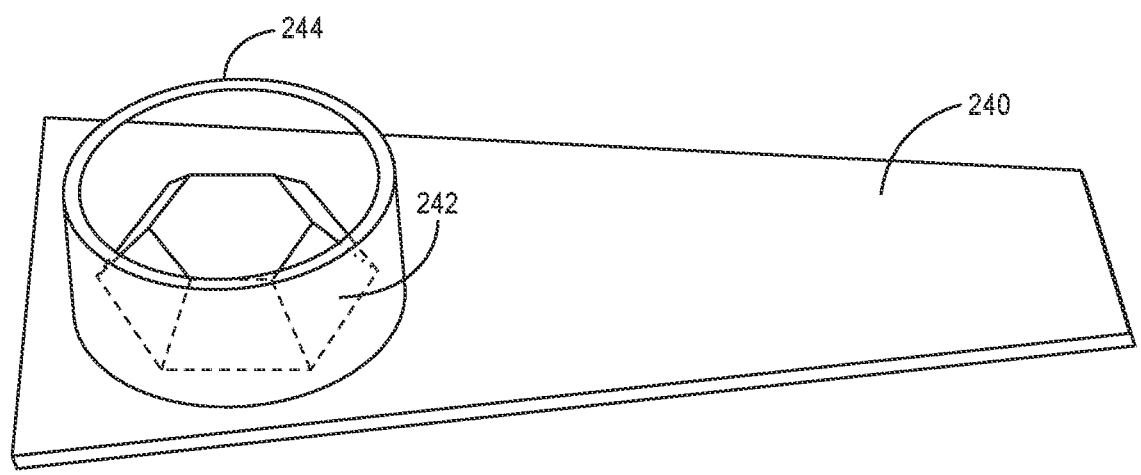
FIGS. 11A-11D illustrate other embodiments of a pre-packaged RTSE/vaporizable formulation providing individual use dosages and packaging techniques in accordance with the present invention. 11A illustrates a protective bubble which is removed prior to use; 11B illustrates the applicator-tab suitable for immediate use after the bubble has been removed; 11C illustrates a circular or array format for packaging a plurality of applicator-tabs, and 11D illustrates another embodiment of an applicator-tab having a channel to control flow of melted RTSE.
Figure 11B:
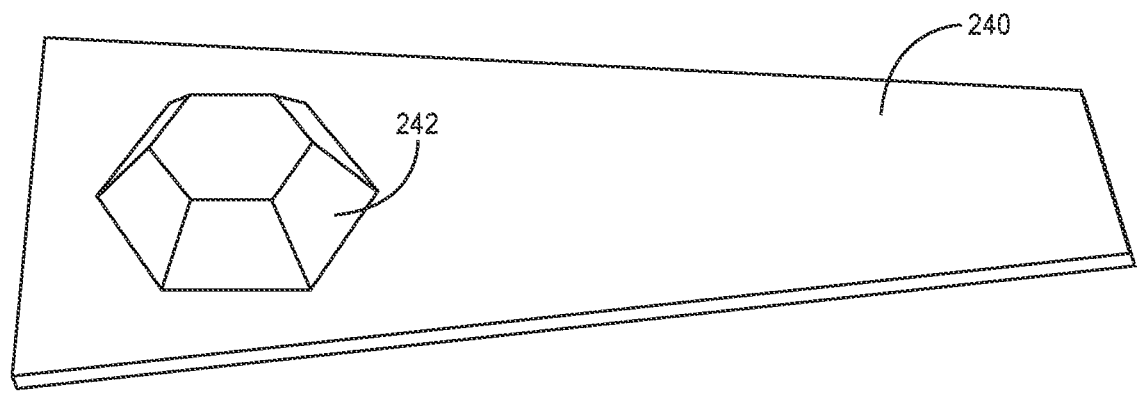

FIGS. 11A-11B illustrates an applicator-tab embodiment providing a pre-loaded, disposable/recyclable dab tool to facilitate vaporizer loading with a consistent/uniform dose of RTSE or another vaporizable formulation. A hand-graspable substrate 240 defines an applicator portion for carrying a tab or dose of RTSE 242. The substrate 240 can be formed from a variety of materials, including but not limited to, metal, paper products, hemp paper, parchmentized cellulose, ceramic, and glass. Embodiments of substrate 240 include one or more features of being chemically inert, heat stable, nontoxic, recyclable, malleable, non-stick, and relatively rigid to support dispensing of the RTSE 242. FIG. 11A illustrates a protective bubble 244 over tab 242 which is removed prior to use. Bubble 244 may be formed from a film material secured to substrate 240. FIG. 11B illustrates the applicator-tab suitable for immediate use after the bubble 244 has been removed.

In one intended method of use, the applicator-tab is used with a vaporizer specifically designed to receive the applicator tab product. In one case, a user will press the shaped tab 242 into the similarly-shaped indentation in the vape adapted to receive the particular tab 242. In this case, the applicator substrate 240 does not need to be heat stable as it is removed after the tab is released.

In another intended method of use, the applicator tab is a substitute for a dab tool. In one case the user will apply the applicator tab to a preheated (400-700° F.) vaporizer bowl. In this case the applicator substrate must be heat stable.

Figure 11C:
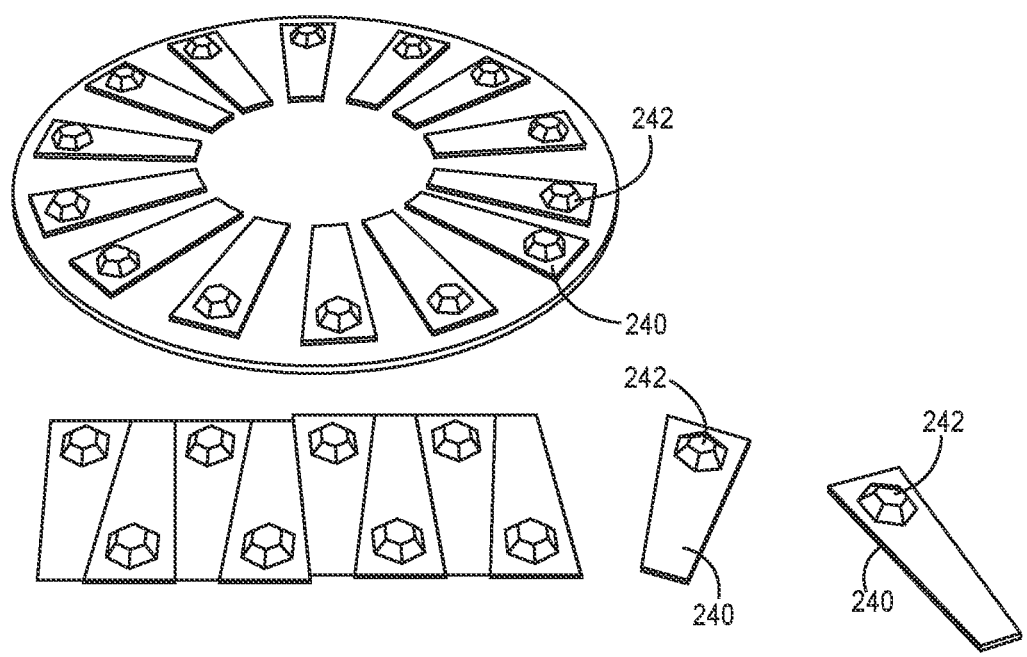

FIG. 11C illustrates a packaged plurality of applicator-tab embodiments. A plurality of applicator-tabs may be initially secured together and adapted to be individually released prior to use. For example, a plurality of applicator tabs could be provided in circular or arrayed formats as illustrated. In another example, a plurality of applicator-tabs are provided within a bottle or other container, such as a child-resistant container.

Figure 11D:
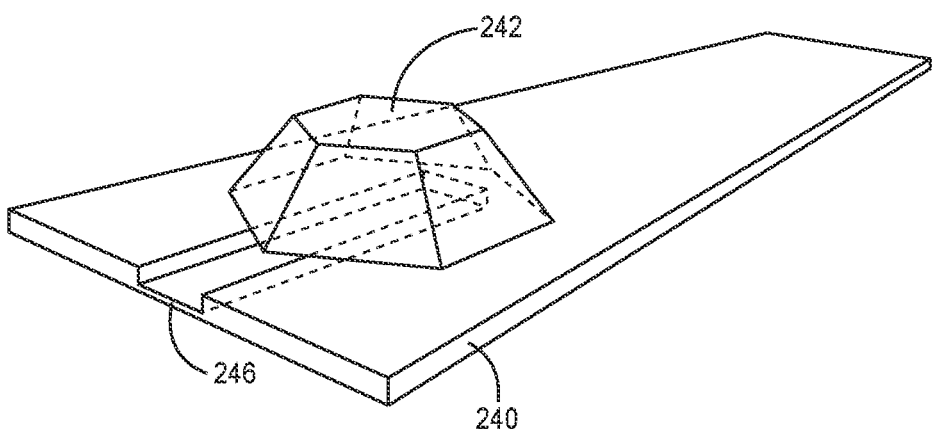

FIG. 11D illustrates another embodiment of an applicator-tab wherein the substrate 240 includes a defined channel 246. The channel 246 functions to control a flow of melted RTSE, such as upon preheated vaporizer bowl use. Channel 246 may be defined upon or within the substrate 240. In another embodiment, the substrate is formed into a concave or spoon-like shape to control the flow of melted RTSE.

The individual use portion end of the applicator tab can be treated with a non-stick substance, such as PTFE, to facilitate the reversibility of the fixation of the vaporizable extract to the applicator tab.

The individual use portion end of the applicator tab further comprises an indentation of suitable depth and shape to hold the individual use portion of the vaporizable extract. For example, a hex-shaped depression may be defined into the substrate 240 and sized to receive a single dose of hex-shaped RTSE. In another embodiment, a channel is in communication with the indentation such that when the vaporizable extract is heated and melts the melted vaporizable extract will flow into the channel.

While the present disclosure includes many embodiments shown and described in detail, various modifications and improvements thereon will become readily apparent to those skilled in the art. Accordingly, the spirit and scope of the present invention is not to be limited by the foregoing examples, but is to be understood in the broadest sense allowable by law.

With respect to the above, it is to be understood that the invention is not limited in its application to the details of construction and to the arrangement of the components listed or the steps set forth in the description or illustrated in the drawings. The various apparatus and methods of the disclosed invention are capable of other embodiments, and of being practiced and carried out in various ways that would be readily known to those skilled in the art, given the present disclosure. Further, the terms and phrases used herein are for descriptive purposes and should not be construed as in any way limiting.

As such, those skilled in the art will appreciate that the conception upon which this disclosure is based may be utilized as a basis for designing other inventions with similar properties. It is important therefore that the embodiments, objects, and claims herein, be regarded as including such equivalent construction and methodology insofar as they do not depart from the spirit and scope of the present invention.

What is claimed is:

1. An assembly comprising:
    at least one individual use portion of a vaporizable room temperature solid extract affixed to an elongated applicator tab, wherein one end of the applicator tab defines a grasping handle and with the vaporizable extract being releasably affixed at an opposite end of the applicator tab; and
    wherein the opposite end of the applicator tab further comprises a channel in communication with the vaporizable extract such that when the vaporizable extract is heated, a melted vaporizable extract flows into the channel and is directed toward a channel end.

2. The assembly according to claim 1 wherein the applicator tab includes a non-stick surface to facilitate releasability of the fixation of the vaporizable extract to the applicator tab.

3. The assembly of claim 1 wherein the opposite end of the applicator tab further comprises an indentation sized to receive the at least one individual use portion of the vaporizable extract.

4. The assembly of claim 3 wherein the channel is in communication with the indentation such that when the vaporizable extract is heated and melts the melted vaporizable extract will flow into the channel.

5. The assembly of claim 3 wherein the indentation and the at least one individual use portion of the vaporizable extract include a plurality of faceted surfaces.

6. The assembly of claim 1 wherein a plurality of applicator tabs are secured together with each being adapted to be individually released prior to use.

7. The assembly of claim 6 wherein the applicator tabs are secured together in a circular format.

8. An applicator tab for a vaporizable extract comprising:
an elongated substrate including one end defining a grasping handle and with an individual use portion of the vaporizable extract being secured at an opposite end of the substrate and released for consumption after the substrate is repositioned to a heating chamber of a vaporizer; and
a channel at an opposite end of the substrate, with the channel directing a melted liquid toward an end of the substrate to facilitate pouring of the melted liquid into the heating chamber.

9. The applicator tab of claim 8 further comprising an indentation in the substrate sized to receive the individual use portion.

10. The applicator tab of claim 9 wherein the indentation in the substrate and the vaporizable extract each include faceted surfaces.

11. The applicator tab of claim 8 further comprising a bubble or film overlay covering the individual use portion.

12. The applicator tab of claim 8 wherein a plurality of elongated substrates are initially secured together in an arrayed or circular or other format, with individual substrates being separated from the plurality prior to use.

13. The applicator tab of claim 8 wherein the channel extends from an indentation in the substrate sized to receive the vaporizable extract toward an edge of the substrate.

14. A method of delivering an individual dose of a vaporizable extract, comprising:
providing a plurality of applicator tab segments each having a graspable handle and carrying an individual use portion of a vaporizable room temperature solid extract;
separating one applicator tab from the plurality of applicator tab segments;
delivering said one of the plurality of applicator tab segments to a vaporizer; and
releasing the vaporizable extract from the applicator tab segment of the plurality of applicator tab segments and into a heating unit of the vaporizer.

15. The method of claim 14 wherein the plurality of applicator tab segments are initially connected together and said separating includes disconnecting substrate material of adjacent applicator tab segments.

16. The method of claim 14 wherein said releasing the vaporizable extract portion includes melting and flowing a melted extract portion through a channel defined at one end of the applicator tab segments.

17. The method of claim 14 wherein each individual use portion is held within a depression of a substrate material.

18. The method of claim 17 wherein the depression and individual use portion include a plurality of faceted surfaces, with multiple faceted surfaces of the individual use portion contacting multiple faceted surfaces of the depression when the individual use portion is held by the applicator tab segment of the plurality of applicator tab segments.

* * * * *